(12) United States Patent
Zang

(10) Patent No.: US 11,315,187 B2
(45) Date of Patent: Apr. 26, 2022

(54) INFORMATION ALERTS METHOD, APPARATUS AND DEVICE

(71) Applicant: Advanced New Technologies Co., Ltd., Grand Cayman (KY)

(72) Inventor: Yue Zang, Hangzhou (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 80 days.

(21) Appl. No.: 16/806,693

(22) Filed: Mar. 2, 2020

(65) Prior Publication Data

US 2020/0202445 A1    Jun. 25, 2020

Related U.S. Application Data

(63) Continuation of application No. PCT/CN2018/115593, filed on Nov. 15, 2018.

(30) Foreign Application Priority Data

Dec. 29, 2017 (CN) .......................... 201711482381.1

(51) Int. Cl.
    *G06Q 40/06*      (2012.01)
    *G16H 40/67*      (2018.01)
    (Continued)

(52) U.S. Cl.
    CPC ......... *G06Q 40/06* (2013.01); *A61B 5/02055* (2013.01); *A61B 5/1176* (2013.01);
    (Continued)

(58) Field of Classification Search
None
See application file for complete search history.

(56) References Cited

U.S. PATENT DOCUMENTS

| 9,716,964 B1 * | 7/2017 | Sheng ..................... H04W 4/20 |
| 10,460,312 B1 * | 10/2019 | Kurani ................... G06Q 20/36 |

(Continued)

FOREIGN PATENT DOCUMENTS

| CN | 101108125 | 6/2010 |
| CN | 102160794 | 8/2011 |

(Continued)

OTHER PUBLICATIONS

"Enrique Garcia-Ceja, Automatic Stress Detection in Working Environments from Smartphones' Accelerometer Data: A first step, Oct. 14, 2015, Tecnologico de Monterrey, Abstract & p. 4" (Year: 2015).*

(Continued)

*Primary Examiner* — Kito R Robinson
*Assistant Examiner* — Toan Duc Bui
(74) *Attorney, Agent, or Firm* — Fish & Richardson P.C.

(57) ABSTRACT

A preset alert trigger event associated with a wealth management application operated on an electronic device is detected. In response to detecting the preset alert trigger event, the electronic device obtains a physiological characteristic parameter characterizing an emotion of a target user. The electronic device determines that a preset normal emotion fluctuation condition is not satisfied according to the physiological characteristic parameter. In response to determining that the normal emotion fluctuation condition is not satisfied, a risk alert on a wealth management action of the target user performed in the wealth management application is output.

20 Claims, 7 Drawing Sheets

(51) Int. Cl.
  *G16H 10/60* (2018.01)
  *G16H 50/30* (2018.01)
  *G16H 50/70* (2018.01)
  *H04W 4/38* (2018.01)
  *A61B 5/0205* (2006.01)
  *A61B 5/1171* (2016.01)
  *A61B 5/16* (2006.01)
  *A61B 5/00* (2006.01)
  *G06F 3/01* (2006.01)
  *G06K 9/00* (2022.01)
  *A61B 5/369* (2021.01)
  *H04M 1/72454* (2021.01)
  *A61B 5/021* (2006.01)
  *A61B 5/024* (2006.01)

(52) U.S. Cl.
  CPC .............. *A61B 5/165* (2013.01); *A61B 5/369* (2021.01); *A61B 5/4884* (2013.01); *G06F 3/015* (2013.01); *G06K 9/00302* (2013.01); *G16H 10/60* (2018.01); *G16H 40/67* (2018.01); *G16H 50/30* (2018.01); *G16H 50/70* (2018.01); *H04M 1/72454* (2021.01); *H04W 4/38* (2018.02); *A61B 5/021* (2013.01); *A61B 5/024* (2013.01); *H04M 2250/12* (2013.01)

(56) References Cited

U.S. PATENT DOCUMENTS

| | | | | |
|---|---|---|---|---|
| 2008/0040484 | A1* | 2/2008 | Yardley | H04L 67/142 709/227 |
| 2011/0201899 | A1 | 8/2011 | Price et al. | |
| 2015/0100475 | A1* | 4/2015 | Cummings | G06Q 20/108 705/38 |
| 2015/0381547 | A1* | 12/2015 | Mandanapu | H04L 67/34 709/206 |
| 2016/0057619 | A1* | 2/2016 | Lopez | G06F 21/44 380/247 |
| 2016/0344826 | A1* | 11/2016 | Sarma | H04L 67/22 |
| 2017/0007165 | A1* | 1/2017 | Jain | A61B 5/0205 |
| 2017/0116402 | A1* | 4/2017 | Hirabayashi | G06F 21/31 |
| 2018/0032126 | A1* | 2/2018 | Liu | G06K 9/00302 |
| 2018/0077188 | A1* | 3/2018 | Mandyam | H04L 67/42 |
| 2020/0125369 | A1* | 4/2020 | Liang | G06F 9/485 |

FOREIGN PATENT DOCUMENTS

| | | |
|---|---|---|
| CN | 105046496 | 11/2015 |
| CN | 106373012 | 2/2017 |
| CN | 107031653 | 8/2017 |
| CN | 107072541 | 8/2017 |
| CN | 107092881 | 8/2017 |
| CN | 107126203 | 9/2017 |
| CN | 107203938 | 9/2017 |
| CN | 107220246 | 9/2017 |
| CN | 104900006 | 10/2017 |
| CN | 107405072 | 11/2017 |
| CN | 108121448 | 6/2018 |
| TW | 201525925 | 7/2015 |
| TW | I540528 | 7/2016 |

OTHER PUBLICATIONS

Crosby et al., "BlockChain Technology: Beyond Bitcoin," Sutardja Center for Entrepreneurship & Technology Technical Report, Oct. 16, 2015, 35 pages.

International Search Report and Written Opinion in PCT Appln. No. PCT/CN2018/115593, dated Dec. 27, 2018, 9 pages (partial translation).

Nakamoto, "Bitcoin: A Peer-to-Peer Electronic Cash System," www.bitcoin.org, 2005, 9 pages.

PCT International Preliminary Report on Patentability in International Appln No. PCT/CN2018/115593, dated Jun. 30, 2020, 9 pages (with English translation).

* cited by examiner

INFORMATION ALERTS METHOD, APPARATUS AND DEVICE

CROSS-REFERENCE TO RELATED APPLICATIONS

This application is a continuation of PCT Application No. PCT/CN2018/115593, filed on Nov. 15, 2018, which claims priority to Chinese Patent Application No. 201711482381.1, filed on Dec. 29, 2017, and each application is hereby incorporated by reference in its entirety.

TECHNICAL FIELD

The present disclosure relates to the field of computers, and in particular, to an information alert method, an information alert apparatus and a device.

BACKGROUND

With the development of computers, many users choose to invest and manage money through the Internet. With the rise of online investment and wealth management, the assets of many users include stocks, funds and other types, not limited to traditional deposits. For the financial industry, in addition to requiring a high threshold of basic knowledge, it also requires users to establish a good investment mentality. For investment, frequent rising and falling will bring an upset emotion to many new users, and under this emotion, impulse investment, impulse stock selling and other wealth management actions often occur.

SUMMARY

In order to alleviate the problems in the related art, the present disclosure provides an information alert method, an information alert apparatus and a device.

An information alert method, including: when detecting a preset alert trigger event, obtaining a physiological characteristic parameter for characterizing an emotion of a target user; determining whether a preset normal emotion fluctuation condition is satisfied based on the physiological characteristic parameter; and in response to determining that the normal emotion fluctuation condition is not satisfied, performing a risk alert on the wealth management action of the target user.

In an optional implementation, the preset alert trigger event includes one or more of: receiving an instruction to start a wealth management application; receiving an instruction to display a page of a wealth management product; receiving an instruction to perform a wealth management action; when a characteristic indicator of a wealth management product on the currently displayed wealth management product page is not within a preset indicator range, the characteristic indicator includes rising and falling rates or a rate of return; when a risk type of a wealth management product on the currently displayed wealth management product page belongs to a preset risk type.

In an optional implementation, the method is applied to a smart terminal, obtaining a physiological characteristic parameter for characterizing an emotion of a target user includes: obtaining a physiological characteristic parameter for characterizing an emotion of the target user from a wearable device bound to the smart terminal.

In an optional implementation, the physiological characteristic parameter includes one or more of: heart rate, body temperature, blood pressure, palm humidity, brain waves, or a facial image.

In an optional implementation, the physiological characteristic parameters includes one or more of heart rate, body temperature, blood pressure, or palm humidity, and the preset normal emotion fluctuation condition includes: the physiological characteristic parameter is within a normal parameter range; the preset normal parameter range is obtained based on an average value of a physiological characteristic parameter of the user in a specified period; or the preset normal parameter range is obtained based on a physiological characteristic parameter of a user when performing a preset normal type of network behavior; the user includes the target user and/or a user related to the target user, and the relevance includes one or more of the same age group, the same gender, or the same region.

In an optional implementation, the physiological characteristic parameter includes brain waves, and the preset normal emotion fluctuation condition includes: the brain waves having a frequency within a preset normal frequency range, and amplitudes within a preset normal amplitude range.

In an optional implementation, the physiological characteristic parameter includes a facial image, and determining whether a preset normal emotion fluctuation condition is satisfied according to the physiological characteristic parameter includes: performing expression recognition on the facial image to obtain a facial expression of the target user; and determining whether the obtained facial expression is a preset normal type expression.

An information alert apparatus, including: a parameter obtaining module configured to when detecting a preset alert trigger event, obtain a physiological characteristic parameter for characterizing an emotion of a target user; a condition determining module configured to determine whether a preset normal emotion fluctuation condition is satisfied according to the physiological characteristic parameter; an information alert module configured to, in response to determining that the normal emotion fluctuation condition is not satisfied, perform a risk alert on the wealth management action of the target user.

In an optional implementation, the apparatus is provided in a smart terminal, and the parameter obtaining module is configured to, when detecting a preset alert trigger event, obtain a physiological characteristic parameter for characterizing an emotion of a target user from a wearable device bound to the smart terminal.

A computer device including: a processor; and a memory for storing processor-executable instructions; wherein the processor is configured to, when detecting a preset alert trigger event, obtain a physiological characteristic parameter for characterizing an emotion of a target user; determine whether a preset normal emotion fluctuation condition is satisfied according to the physiological characteristic parameter; in response to determining that the normal emotion fluctuation condition is not satisfied, perform a risk alert on the wealth management action of the target user.

Technical solutions according to the examples of the present disclosure can include the following beneficial effects.

In some embodiments of the present disclosure, when detecting a preset alert trigger event, obtaining a physiological characteristic parameter for characterizing an emotion of a target user; determining whether a preset normal emotion fluctuation condition is satisfied according to the physiological characteristic parameter; and in response to determining that the normal emotion fluctuation condition is not satisfied, performing a risk alert on the wealth management action of the target user. The alert can alert the target user to alleviate impulsive wealth management behavior that will cause economic losses to the target user.

It should be understood that the above general descriptions and the below detailed descriptions are merely examples and explanation, and are not intended to limit the present disclosure.

BRIEF DESCRIPTION OF THE DRAWINGS

The accompanying drawings, which are incorporated in and constitute a part of the present disclosure, illustrate examples consistent with the present disclosure and, together with the description to explain the principles of the disclosure.

DETAILED DESCRIPTION OF THE EXAMPLES

Figure 1A:
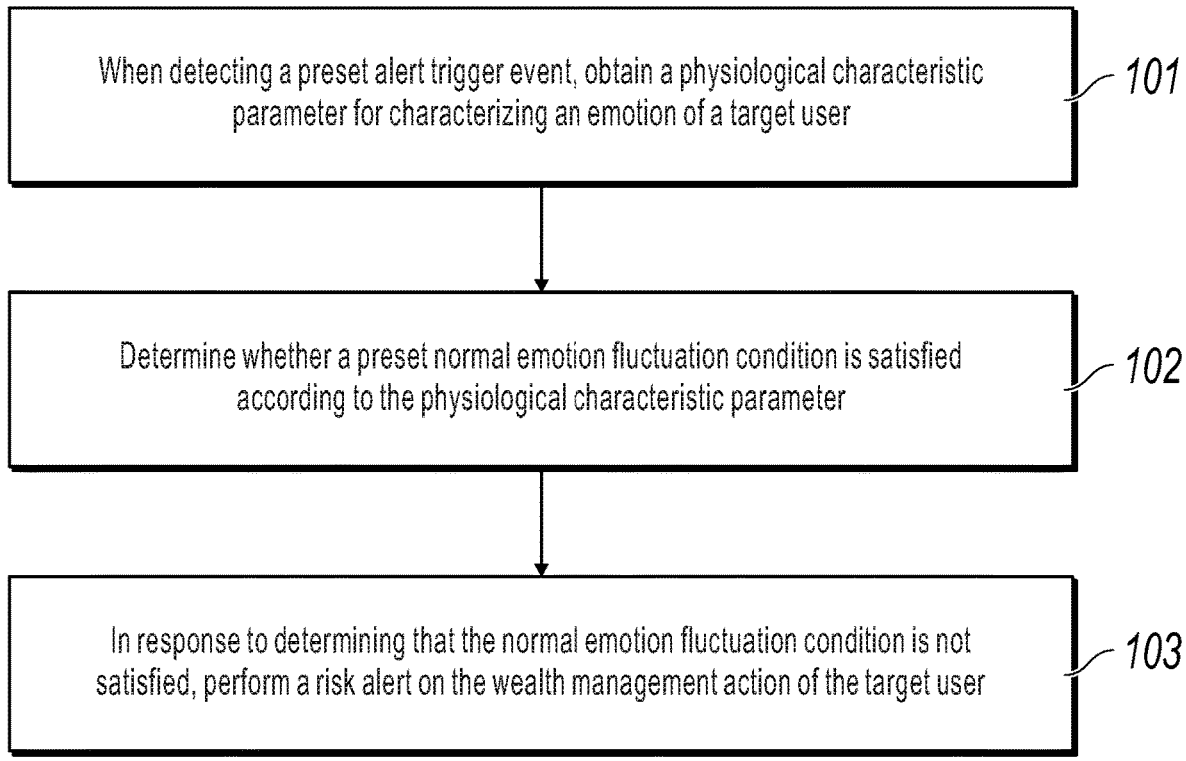
FIG. 1A is a flowchart of an embodiment of an information alert method in the present disclosure.

Examples will be described in detail herein, with the illustrations thereof represented in the drawings. When the following descriptions involve the drawings, same numbers in different drawings refer to same or similar elements unless otherwise indicated. The embodiments described in the following are merely some but not all examples of apparatuses and methods consistent with the present disclosure as detailed in the appended claims.

The terms used in the present disclosure are for the purpose of describing particular examples only, and are not intended to limit the present disclosure. Terms like "a", "the" and "said" in their singular forms in the present disclosure and the appended claims are also intended to include plurality, unless clearly indicated otherwise in the context. It should also be understood that the term "and/or" used herein includes any and all possible combinations of one or more of the associated listed items.

It is to be understood that, although terms "first," "second," "third," and the like may be used in the present disclosure to describe various information, such information should not be limited to these terms. These terms are only used to distinguish one category of information from another. For example, without departing from the scope of the present disclosure, first information may be referred as second information; and similarly, second information may also be referred as first information. Depending on the context, the word "if" herein may be interpreted as "when" or "upon" or "in response to determining".

For the financial industry, in addition to requiring a high threshold of basic knowledge, it also requires users to establish a good investment mentality. In practical applications, decisions and judgments made under abnormal emotions such as anxiety, extreme tension, and uneasiness are often biased, and many users often do not realize that they are in abnormal emotions. If wealth management is dealt at this time, economic losses should not be underestimated.

In order to decrease the disadvantages of wealth management actions that cause losses to users, the present disclosure provides an information alert method. When detecting a preset alert trigger event, a physiological characteristic parameter for characterizing a target user's emotion can be obtained, and then it can be determined whether a preset normal emotion fluctuation condition is satisfied according to the physiological characteristic parameter. If the physiological characteristic parameter does not satisfy the normal emotion fluctuation condition, a risk alert can be performed on the wealth management action of the target user to avoid economic losses caused by the users' wealth management action in abnormal emotions.

Embodiments of the present disclosure will be illustrated below with reference to the drawings.

As shown in FIG. 1A, FIG. 1A is a flowchart of an embodiment of an information alert method in the present disclosure. The method may include the following steps 101 to 103.

At step 101, when detecting a preset alert trigger event, a physiological characteristic parameter for characterizing an emotion of a target user is obtained.

At step 102, it is determined whether a preset normal emotion fluctuation condition is satisfied according to the physiological characteristic parameter.

At step 103, in response to determining that the normal emotion fluctuation condition is not satisfied, a risk alert is performed on the wealth management action of the target user.

Embodiments of the present disclosure may be applied to a smart terminal.

In one example, embodiments can be an application scenario that includes only a smart terminal.

In this scenario, the smart terminal can be an electronic device of any type that can run wealth management software, and the electronic device can be a handheld electronic device or other electronic devices. For example, devices can be a cell phone, a media player or other handheld portable devices, slightly smaller portable devices such as a wristwatch device, a pendant device, or other wearable or miniaturized devices, gaming equipment, a tablet computer, a notebook computer, a desktop computer, a television, a computer or other electronic devices integrated in a computer monitor. It can be seen that, in this application scenario, the method in FIG. 1A can be applied to a mobile terminal or a wearable device, etc., depending on whether the device can collect a physiological characteristic parameter.

In another example, it can be an application scenario including a combination of a smart terminal and a wearable device.

In this scenario, the smart terminal can be electronic devices of any type that can run wealth management software. For example, the smart terminal may be a smart phone, a PDA (Personal Digital Assistant), a media player, a tablet computer, a notebook computer, a desktop computer, a television, a computer integrated in a computer display, or other electronic devices. The wearable device can be a device capable of detecting a physiological characteristic parameter for characterizing the emotion of the user. For example, the wearable device may be a smart bracelet, a helmet capable of detecting brain waves, and the like.

The physiological characteristic parameter may be a characteristic parameter for characterizing a user's emotion. For example, the physiological characteristic parameter can be parameters such as heart rate, body temperature, blood pressure, palm humidity, brain waves, and a facial image. In one example, a parameter such as heart rate, body temperature, blood pressure, and brain waves can be obtained through a wearable device bound to a smart terminal, and a parameter such as a palmar humidity and a facial image can be obtained through a humidity sensor and a camera on the smart terminal.

Figure 1B:
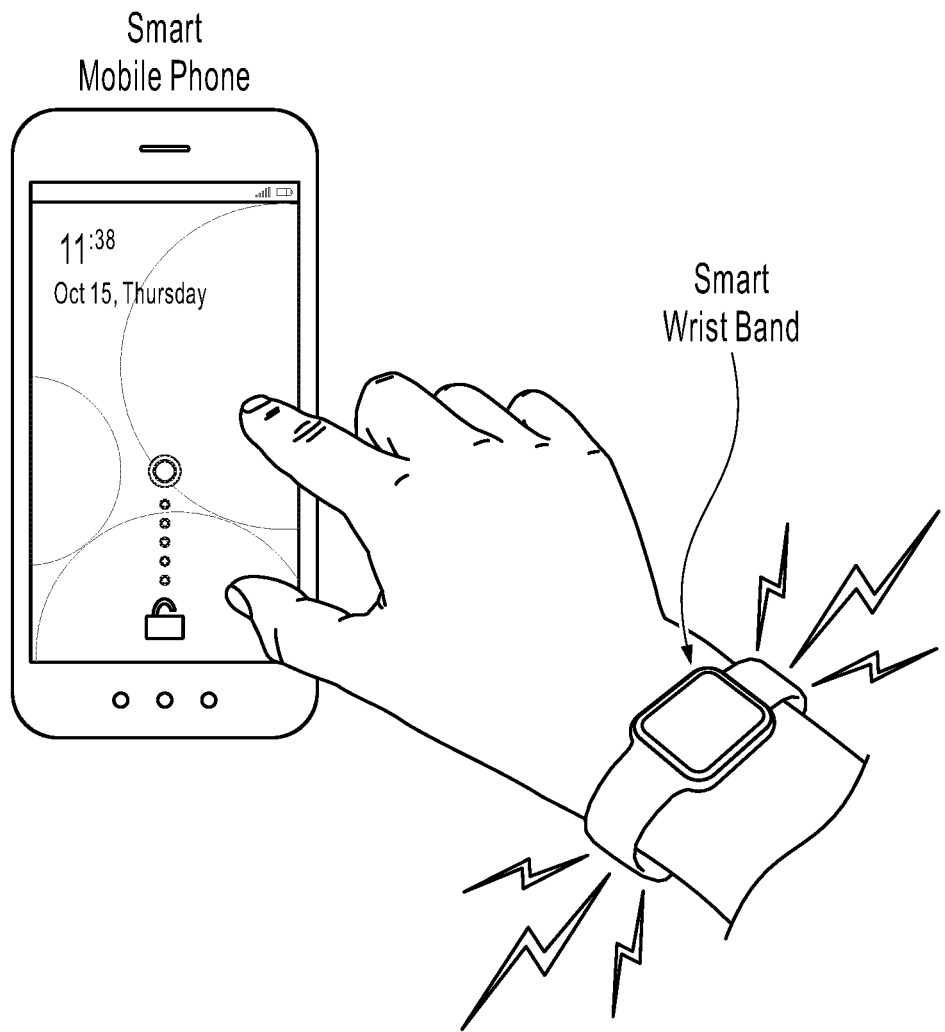
FIG. 1B is a schematic diagram of an application scenario of an information alert method of the present disclosure.

As shown in FIG. 1B, FIG. 1B is a schematic diagram of an application scenario of the information alert method of the present disclosure. In this application scenario, an application scenario where some methods of the present disclosure are applied to a combination of a smart terminal and a wearable device is used as an example. A smart phone is used for a smart terminal as an example, and a smart bracelet is used for a wearable device as an example. If the smart terminal is bound to the wearable device and the smart terminal and the wearable device can communicate, the smart terminal can obtain physiological characteristic parameters for characterizing the emotion of the target user from the wearable device.

In some embodiment of the present disclosure, when detecting a preset alert trigger event, a physiological characteristic parameter for characterizing the emotion of the target user can be obtained.

The target user is the target of emotions to be detected. For example, the target user can be a user who uses a wealth management application to log in to a wealth management platform, or a user who uses a smart terminal, and is referred to as a target user in order to distinguish from other users. The preset alert trigger event can be a preset event for triggering the information alert. Here are some examples of alert trigger events. The alert trigger event can be one of the trigger events or a combination of multiple trigger events. When the alert trigger event is a combination of multiple trigger events, if any of the trigger event is satisfied, the alert trigger event triggers to obtain the physiological characteristic parameter for characterizing the emotion of the target user. Thereby execution of obtaining the physiological characteristic parameter under multiple conditions can be achieved.

A first trigger event: receiving an instruction to start a wealth management application.

A wealth management application can be an application for conducting wealth management action. The target user can click an application icon corresponding to the wealth management application to trigger the generation of an instruction to start the wealth management application, so as to start the wealth management application. The target user starts the wealth management application, which indicates that the target user has a desire to perform wealth management actions. Therefore, the emotion of the target user at this time can be monitored and alerted.

A second trigger event: receiving an instruction to display a page of a wealth management product.

When starting the wealth management application, usually there are a plurality of wealth management products on the homepage, and even other information, and when receiving an instruction to display a page of a wealth management product, specific wealth management product information will be displayed. At this time, the emotion of the target user may change. Therefore, when receiving an instruction to display the page of the wealth management product, the emotion of the target user may be detected and alerted when the target user has abnormal emotions.

A third trigger event: receiving an instruction to perform a wealth management action.

The wealth management action can include a buying action, a selling action, etc. For example, buying or selling stocks, funds, etc. when receiving a user's instruction to perform a wealth management action, it is clear that the user has a willingness to perform a wealth management action. If the target user is in abnormal situations such as extreme tension and anxiety at this time, the wealth management action may be improper, so the target user can be alerted of the current emotion of the target user.

A fourth trigger event: a characteristic indicator of the wealth management product on the currently displayed wealth management product page is not within a preset indicator range, and the characteristic indicator includes rising and falling rates or a rate of return.

A characteristic indicator can be an indicator used to describe the characteristics of a wealth management product, which are generally reference factors for the user to decide whether to perform a wealth management action. For example, the characteristic indicator can be rising and falling rates of a stock, or the return rate of a fund. Too large or too low rising and falling rates or a too high or too low return rate may cause changes in the target user's emotion, especially for some beginner investors, emotions may change a lot. Therefore, the emotion of the target user can be monitored and alerted when the emotion is abnormal to avoid target users making wrong choices when a characteristic indicator of a wealth management product is too high or too low.

A fifth trigger event: a risk type of a wealth management product on the currently displayed wealth management product page is a preset risk type.

In one example, wealth management products can be divided based on risks. For example, wealth management products can be divided into low-risk types, medium-risk types, and high-risk types. The specific dividing method can be set flexibly.

The risk types preset in the present implementation can be determined based on the current wealth management action to be performed. For example, if the wealth management action is a selling action, the preset risk type can be a low-risk type so that the user can be alerted whether to sell the low-risk type of wealth management product to avoid selling a wealth management product of a low-risk type under abnormal emotions that would bring economic loss to the target user. If the wealth management action is a buying action, the preset risk type can be a high-risk type so that the user can be alerted whether to buy the high-risk type of wealth management product to avoid buying a wealth management product of a high-risk type under abnormal emotions that would bring economic loss to the target user.

It can be understood that the preset alert trigger event can also be other alert trigger events. As long as the event needs to monitor and alert the target user's emotions. Details are omitted here for simplicity.

When detecting a preset alert trigger event, a physiological characteristic parameter for characterizing the emotion of the target user can be obtained. When detecting a preset alert trigger event, the physiological characteristic parameter can be obtained only once, that is, the current physiological characteristic parameters can be obtained to detect the emotion of the target user when the alert trigger event occurs; or it is also possible to obtain the physiological characteristic parameter at a specified frequency starting from the time when the preset trigger event is detected, to detect the emotion of the target user after the alert trigger event occurs.

In one example, after a preset stop monitoring event occurs, monitoring the target user's emotion can be stopped. The preset stop monitoring event may be one or more events of receiving an instruction to close a wealth management application, receiving an instruction to close a displayed page of a wealth management product, or receiving an instruction to cancel a wealth management action and the like. It can be seen that when a preset stop monitoring event occurs, monitoring the target user's emotion can be stopped to realize automatic stopping monitoring.

After obtaining the physiological characteristic parameter for characterizing the emotion of the target user, it can be determined whether the preset normal emotion fluctuation condition is satisfied according to the physiological characteristic parameter, and then, if the preset normal emotion fluctuation condition is not satisfied, risk alert is issued for the wealth management action of the target user.

The preset normal emotion fluctuation condition may be a preset condition for determining that the user is in a normal emotion fluctuation. For different physiological characteristic parameters, the preset normal emotion fluctuation conditions are different.

In one example, taking one or more of physiological characteristic parameters including heart rate, body temperature, blood pressure, or palm humidity as examples, the preset normal emotion fluctuation condition includes: the physiological characteristic parameter is within a normal parameter range. Correspondingly, if the physiological characteristic parameter is within the preset normal parameter range, the normal emotion fluctuation condition is satisfied, and if the physiological characteristic parameter is not within the preset normal parameter range, the normal emotion fluctuation condition is not satisfied. Under abnormal emotions such as nervousness and excitement, the user's heart rate tends to rise; body temperature may rise or fall; blood pressure may rise; palm humidity may also increase. For each physiological characteristic, a corresponding normal parameter range can be set, such as a normal heart rate parameter range, a normal body temperature parameter range, and a normal blood pressure parameter range. Therefore, when the physiological characteristic parameter is not within the normal parameter range, it can be determined that the normal emotion fluctuation condition is not satisfied. The physiological characteristic parameter can include one of heart rate, body temperature, blood pressure, and palm humidity, and can also include a plurality of combined parameters. When the physiological characteristic parameter includes a plurality of combined parameters, in one example, it is possible that when each of the combined parameters is within the corresponding normal parameter range, it is determined that the normal emotion fluctuation condition is satisfied. Therefore, combined determination can be achieved and the accuracy in determining an emotion can be improved. In another example, when each physiological characteristic parameter in the combined parameters is within the corresponding normal parameter range, it can be determined that the normal emotion fluctuation condition is satisfied, so that any physiological characteristic parameter can be used to determine the user's emotion.

It can be seen that, in the present implementation, by determining whether the physiological characteristic parameter is within a preset normal parameter range, emotion determining can be implemented and the determining efficiency can be improved.

Regarding the preset normal parameter range, in an optional implementation, the preset normal parameter range is obtained based on an average value of a physiological characteristic parameter of the user in a specified period.

Regarding the user, the user may be the target user, so that the normal parameter range is obtained based on the average value of the physiological characteristic parameter of the target user in a specified period. The user can also be users who are related to the target user, so that the normal parameter range is obtained based on the average value of the physiological characteristic parameters of the related users in a specified period. The so-called relevance may be similarity or correlation, so that the physiological characteristic parameters of the related users are applicable to the target user. For example, the relevance can belong to one or more of the same age group, the same gender, the same nationality, or the same city, etc., so that the physiological characteristic parameters of the related user can be used as reference for the target user.

Regarding the specified period, the specified period may be a time period specified in advance. For example, the specified period can be one day, one week, and so on. In order to improve the accuracy of the determination, the specified period can be a certain period of time in the near future, for example, the specified period can be the previous day, the previous week, or the like. For example, the heart rate of the target user in the last day or a period of time can be recorded and saved to obtain an average heart rate. The physiological characteristic parameter in the specified period can be a physiological characteristic parameter detected in the specified period.

After calculating the average value of physiological characteristic parameters within a specified period, the average value can be adjusted according to an adjustment parameter corresponding to the physiological characteristic parameter to obtain a normal parameter range. For different physiological characteristic parameters, the adjustment parameters for adjusting the average values are different. The adjustment parameter can be an adjustment ratio or an adjustment amplitude value, which is specifically set according to requirements. The sizes of the adjustment parameters depend on a normal emotional response when a person sees a wealth management product to avoid determining normal emotions as abnormal emotions. The sizes of the adjustment parameters can also be determined according to the controlling intensity on the emotion. If wishing to alert a small emotional fluctuation, the adjustment parameter can be set to a small value. If wishing to alert a relatively large emotional fluctuation, the adjustment parameter can be set to a relatively large value. The adjustment parameter can also be set based on an instruction of the target user.

It can be seen that the preset normal parameter range in the present implementation is obtained based on the average value of the physiological characteristic parameter of the user in a specified period, which can improve the efficiency of obtaining the normal parameter range.

In another optional implementation, the preset normal parameter range is obtained based on a physiological characteristic parameter of a user when performing a preset normal type of network action.

Here, the preset normal type of network action can be a network action that does not cause large fluctuations in user's emotion. For example, browsing web pages, retrieving information, and other network actions.

Regarding the user, the user can be the target user, so that the normal parameter range is obtained based on the physiological characteristic parameters of the target user when performing a preset normal type of network action. The user can also be users related to the target user, so that the normal parameter range is obtained based on the physiological characteristic parameters of the related users when performing the preset normal type of network action. The so-called relevance can be similarity or correlation, so that the physiological characteristic parameters of the related users are applicable to the target user. For example, the relevance can belong to one or more of the same age group, the same gender, the same nationality, or the same city, etc., so that the physiological characteristic parameters of the related user can be used for reference for the target user.

After obtaining the physiological characteristic parameters when the user performs a preset normal type of network action, the normal parameter range can be determined according to the average value of the obtained physiological characteristic parameters, or the normal parameter range can be determined according to a maximum and minimum values of the obtained physiological characteristic parameters. For example, the obtained average value can be adjusted according to the adjustment parameter corresponding to the physiological characteristic parameter to obtain a normal parameter range. For different physiological characteristic parameters, the adjustment parameters for adjusting the average values are different. The adjustment parameter can be an adjustment ratio or an adjustment amplitude value, which is specifically set according to requirements. The sizes of the adjustment parameters depend on a normal emotional response when a person sees a wealth management product to avoid determining normal emotions as abnormal emotions. The sizes of the adjustment parameters can also be determined according to the controlling intensity on the emotion. If wishing to alert a small emotional fluctuation, the adjustment parameter can be set to a small value. If wishing to alert a relatively large emotional fluctuation, the adjustment parameter can be set to a relatively large value.

It can be seen that in the present implementation, the normal parameter range can be determined according to a preset normal type of network action, in order to compare the wealth management action with the normal type of network action, physiological characteristic parameters of a normal type of network action is used to determine physiological characteristic parameters of wealth management action.

In another optional implementation, determining whether a preset normal emotion fluctuation condition is satisfied according to the physiological characteristic parameter can include: determining a parameter change value of the target user according to the physiological characteristic parameter, and determining whether the change value is within a preset normal parameter variation range. If the parameter change value is within the preset normal parameter variation range, it is determined that the normal emotion fluctuation condition is satisfied, otherwise, it is determined that the normal emotion fluctuation condition is not satisfied. It can be seen that, in the present implementation, by comparing the parameter change value of the target user with a preset normal parameter variation range, so determination of normal emotion fluctuation condition is realized.

The preset normal parameter variation range can be obtained based on the average value of the physiological characteristic parameter when the user sees a specified wealth management product.

The specified wealth management product can be a product that has the same characteristic indicator of the wealth management product as that of the wealth management product in the currently displayed page or has a difference in the characteristic indicator within a specified range from that of the wealth management product in the currently displayed page. For example, the preset normal parameter variation range can be obtained based on an average value of physiological characteristic parameters when a user sees a high-return-rate or a high-value-added wealth management product.

The user includes a target user, and/or a user related to the target user, and the relevance includes one or more of the same age group, the same gender, the same nationality, or the same city, etc.

Further, in order to improve the accuracy of the normal parameter variation range, the related users can be users with rich investment experience, so that this type of users can be calm in various situations and emotions will not greatly fluctuate.

Further, in order to improve the accuracy of the normal parameter variation range, the physiological characteristic parameter when the user sees the specified wealth management product can be a physiological characteristic parameter in a labeled history record. For example, in all historical records, historical records determined to be normal emotion fluctuations can be labeled, so as to achieve a normal parameter variation range with high accuracy.

In another optional implementation, the physiological characteristic parameters include brain waves, and the preset normal emotion fluctuation condition includes: the brain waves having a frequency within a preset normal frequency range, and amplitudes within a preset normal amplitude range.

Here, brain waves are a method to record brain activity using electrophysiological indicators. When the brain is active, brain waves are generated by summing up postsynaptic potentials that are generated from synchronization of a large number of neurons. It records the changes of radio waves during brain activity, which is the overall reflection of the electrophysiological activities of brain nerve cells on the cerebral cortex or scalp surface. In general, the alpha wave has a frequency of 8 to 13 Hz (the average is 10 Hz) and an amplitude of 20 to 100 μV. It is the basic rhythm of normal human brain waves. If there is no external stimulation, the frequency is quite steady. This rhythm is most obvious when a person is awake, quiet, and with eyes closed. The beta wave has a frequency of 14 to 30 Hz and an amplitude of 100 to 150 μV. The beta wave appears when a person is nervous and emotional or excited, and when someone wakes up from a nightmare, the original slow-wave rhythm can be immediately replaced by such rhythm. Therefore, a normal frequency range and a normal amplitude range can be determined according to different wavebands of the brain waves, so as to determine whether the normal emotion fluctuation condition is satisfied.

In another optional implementation, the physiological characteristic parameter includes a facial image, and determining whether a preset normal emotion fluctuation condition is satisfied according to the physiological characteristic parameter can include: performing facial expression recognition on the image to obtain the facial expression of the target user; and determining whether the facial expression obtained is a preset normal type of expression.

When the user is in abnormal emotions, the facial expression often changes. Therefore, by recognizing the facial expression of the target user, it can be determined whether the target user is in an abnormal emotional state.

It should be understood that other preset methods can also be used to determine whether the preset normal emotion fluctuation condition is satisfied, details are omitted here for simplicity.

Figure 1C:
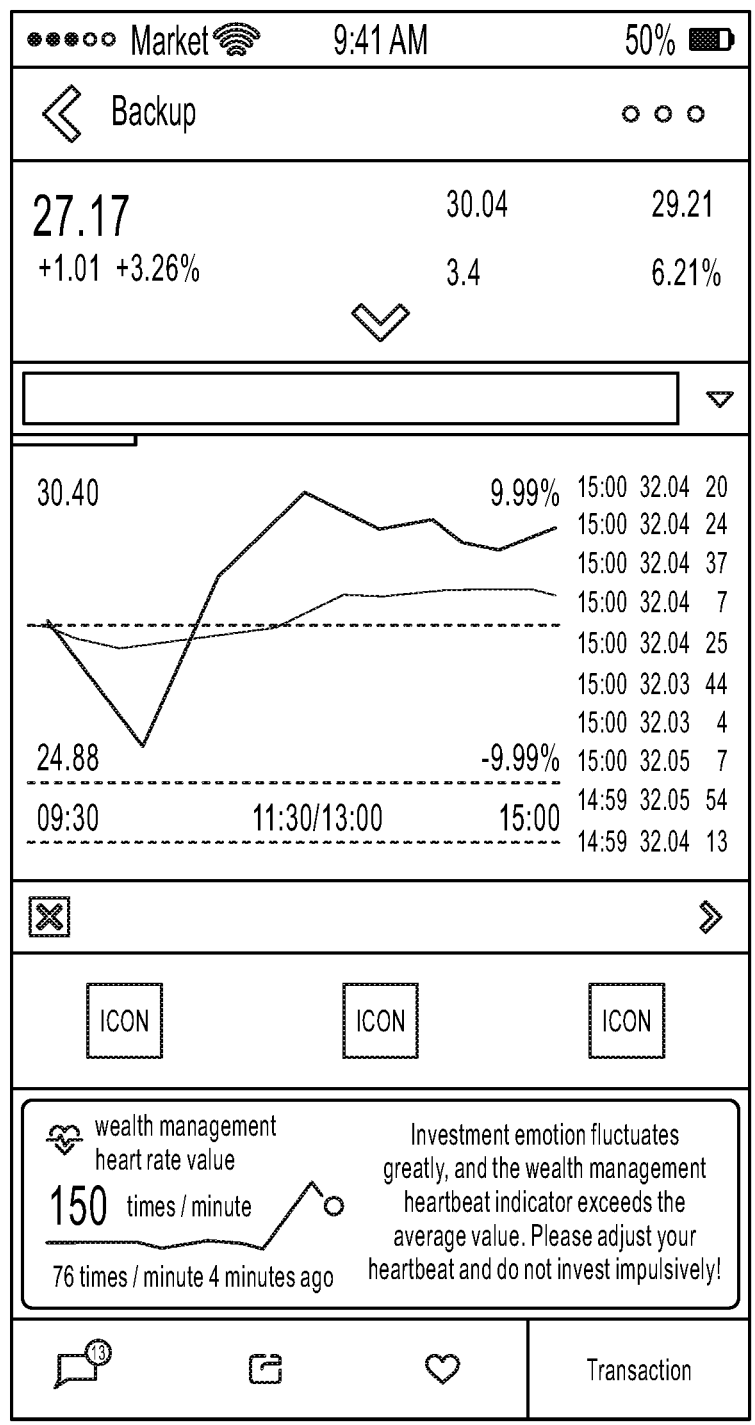
FIG. 1C is a schematic diagram of a risk alert interface according to an example embodiment of the present disclosure.

In response to determining that the normal emotion fluctuation condition is not satisfied, a risk alert is provided for the wealth management action of the target user. The alert method can include a display alert, an audio alert, and the like, and the display alert can include a text alert, a graphic alert, and the like. For example, a display on the current display page is used to alert the target user whether the wealth management action is continued under the current emotion. As shown in FIG. 1C, FIG. 1C is a schematic diagram of a risk alert interface according to an implementation of the present disclosure. In this diagram, the average value is taken as the normal parameter range. Since the heart rate value is greater than the average value, indicating that the user is in abnormal emotions, the heart rate information can be displayed: "150 times/minute", "76 times/minute four minutes ago", and a heart rate change graph is displayed, an alert message "Investment emotion fluctuates greatly, and the wealth management heartbeat indicator exceeds the average value. Please adjust your heartbeat and do not invest impulsively!" is displayed. It can be seen that by sending out an alert message and displaying a heart rate change graphic, the user can be more visually alerted whether to perform wealth management actions to avoid economic losses caused by impulse investments.

In one example, the risk alert can also be cancelled if a condition for canceling the risk alert is satisfied. For example, as the user calms down, when the obtained physiological characteristic parameter satisfies a preset normal emotion fluctuation condition, the risk alert can be cancelled. For another example, when the risk alert time reaches a preset time threshold, the risk alert can be canceled. It can be seen that canceling the risk alert when the condition for canceling the risk alert is satisfied can avoid the visual confusion caused by the constant alerts.

In one example, not only the risk alert can be performed through the smart terminal, but also the alert instruction can be sent to the wearable device bound to the smart terminal if it is determined that the normal emotion fluctuation condition is not satisfied. The alert instruction is used to instruct the wearable device to perform a risk alert on the wealth management action of the target user. The wearable device can implement risk alert through vibration alert, ringtone alert, and display alert.

Figure 1D:
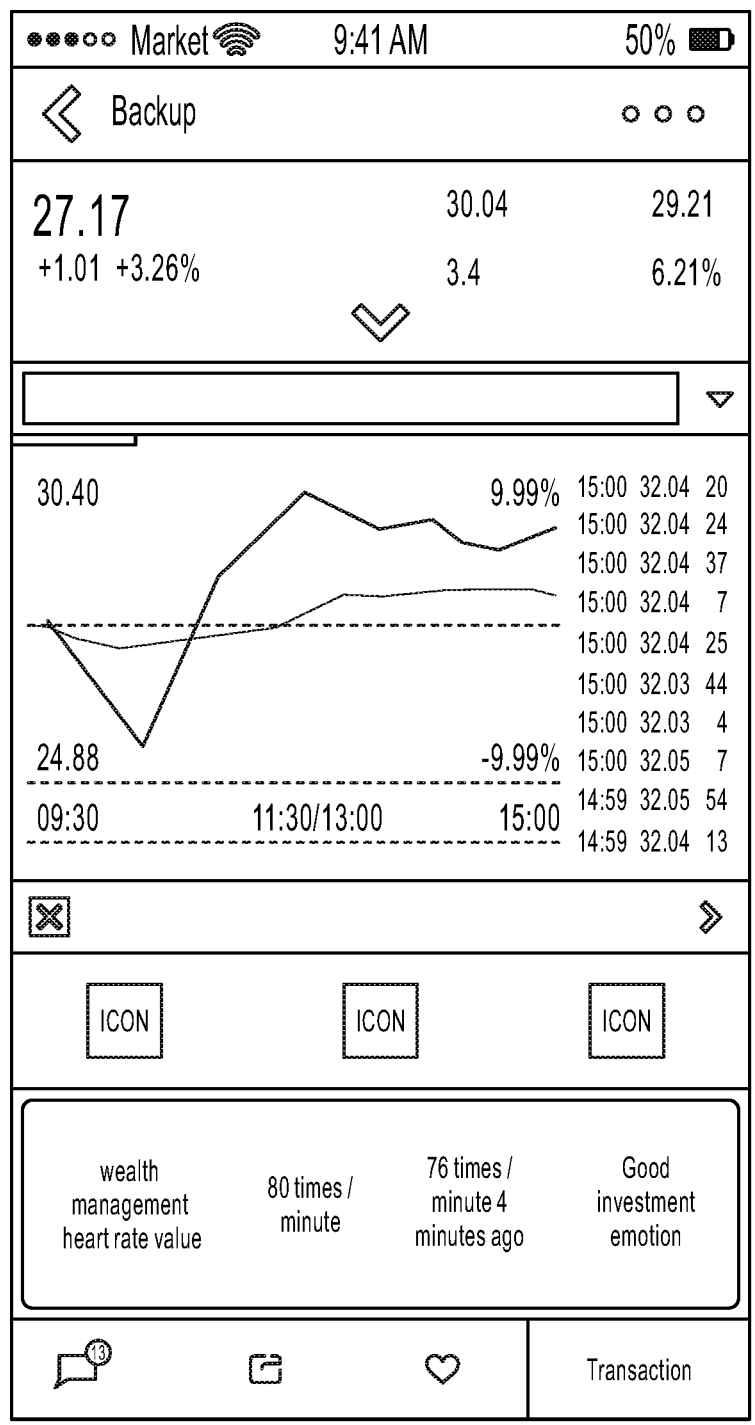
FIG. 1D is a schematic diagram of a normal alert interface according to an example embodiment of the present disclosure.

In one example, in response to determining that the normal emotion fluctuation condition is satisfied, the target user can be normally alerted of the wealth management action. As shown in FIG. 1D, FIG. 1D is a schematic diagram of a normal alert interface according to an implementation of the present disclosure. In the present implementation, the heart rate value is within a normal parameter range, so the heart rate information is displayed: "wealth management heart rate value 80 times/minute", "76 times/minute 4 minutes ago", and an alert message: "Good investment emotion".

Various technical features in the above embodiments can be flexibly combined, as long as there is no conflict or contradiction in the combination of features, which is not described one by one for brevity. Therefore, any combination of the various technical features in the above embodiments is also within the scope of this disclosure.

Figure 2:
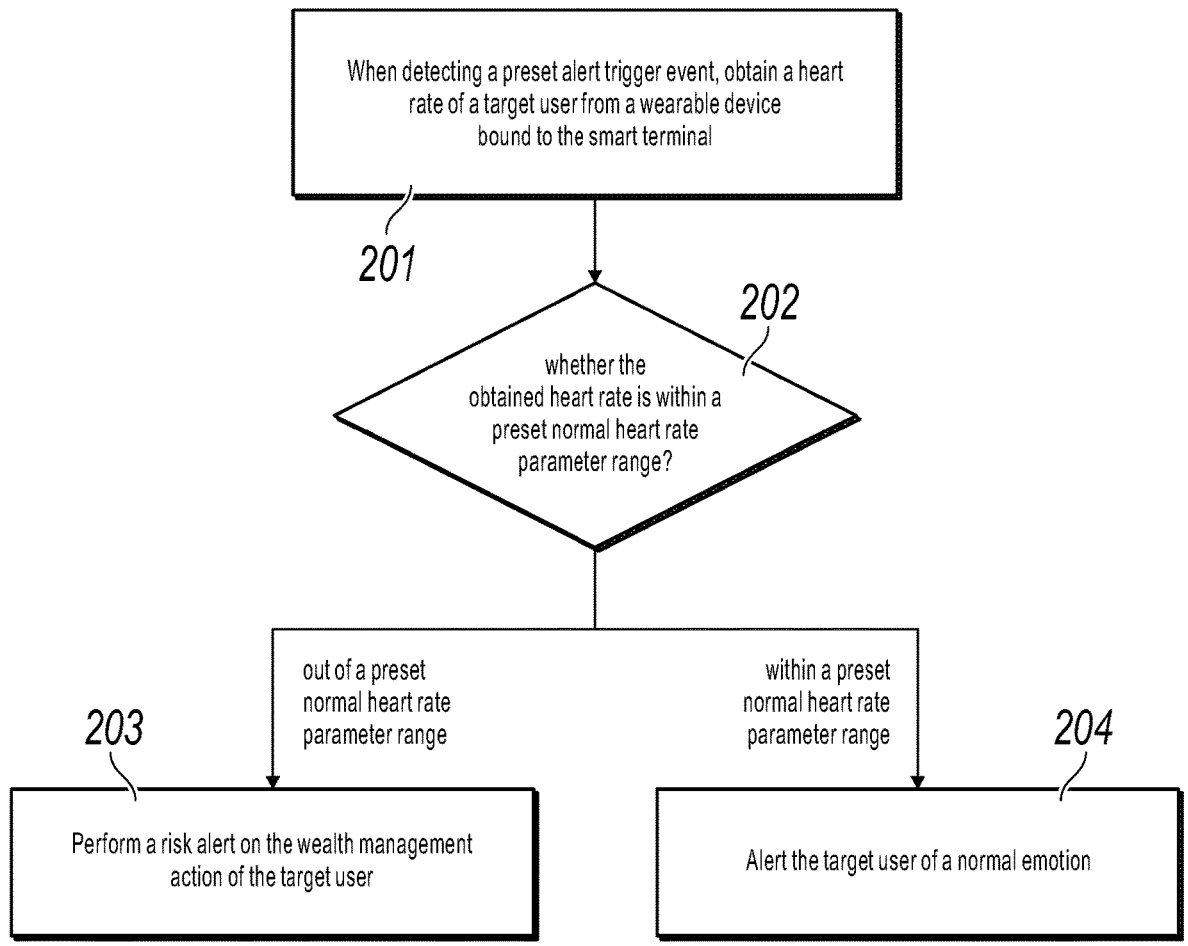
FIG. 2 is a flowchart of another embodiment of an information alert method in the present disclosure.

The following uses one of the combinations as an example. As shown in FIG. 2, FIG. 2 is a flowchart of another embodiment of an information alert method in the present disclosure. The method can be applied to a smart terminal and includes the following steps 201 to 204.

At step 201, when detecting a preset alert trigger event, a heart rate of a target user is obtained from a wearable device bound to the smart terminal.

At step 202, it is determined whether the obtained heart rate is within a preset normal heart rate parameter range.

At step 203, if it is not within the preset normal heart rate parameter range, a risk alert is performed on the wealth management action of the target user.

At step 204, if the target user is within the preset normal heart rate parameter range, the target user is alerted of a normal emotion.

Here, related technology in FIG. 2 is similar to the related technology in FIG. 1A, which is omitted here for simplicity.

As can be seen from the above embodiments, by monitoring the user's emotion, in order to realize the risk alert of the user's wealth management action when abnormal emotions are found in the wealth management scenario, to avoid economics loss to the user by the execution of the wealth management action under abnormal emotions.

Corresponding to the above embodiment of the information alert method, the present disclosure also provides embodiments of the information alert apparatus and an electronic device to which the embodiments are applied.

Figure 3:
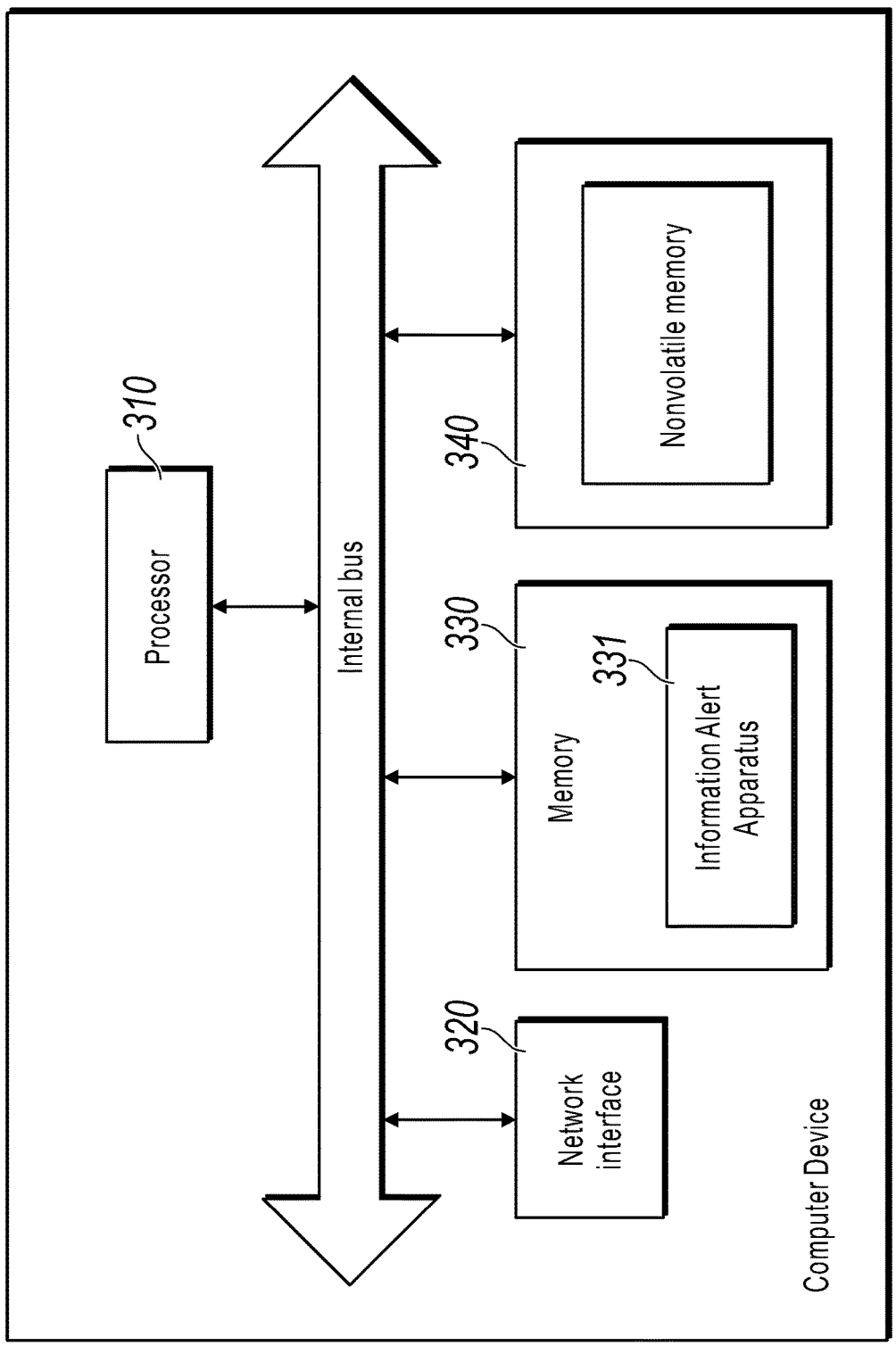
FIG. 3 is a hardware structure diagram of a computer device where an information alert apparatus of the present disclosure is located.

The embodiments of the information alert apparatus of the present disclosure can be applied to a computer device. The apparatus embodiment can be implemented by software, hardware or a combination of software and hardware. Taking software implementation as an example, as an apparatus in a logical sense, it is formed by reading the corresponding computer program instructions in the non-volatile memory into the memory and running through the processor of the computer device where the software is located. In terms of hardware, as shown in FIG. 3, which is a hardware structure diagram of the computer device where the information alert apparatus 331 of the present disclosure is located, in addition to the processor 310, the memory 330, the network interface 320, and the non-volatile memory 340 shown in FIG. 3, the computer device in which the apparatus 331 is located in some embodiments can generally include other hardware according to the actual function of the device, details are omitted here for simplicity.

Figure 4:
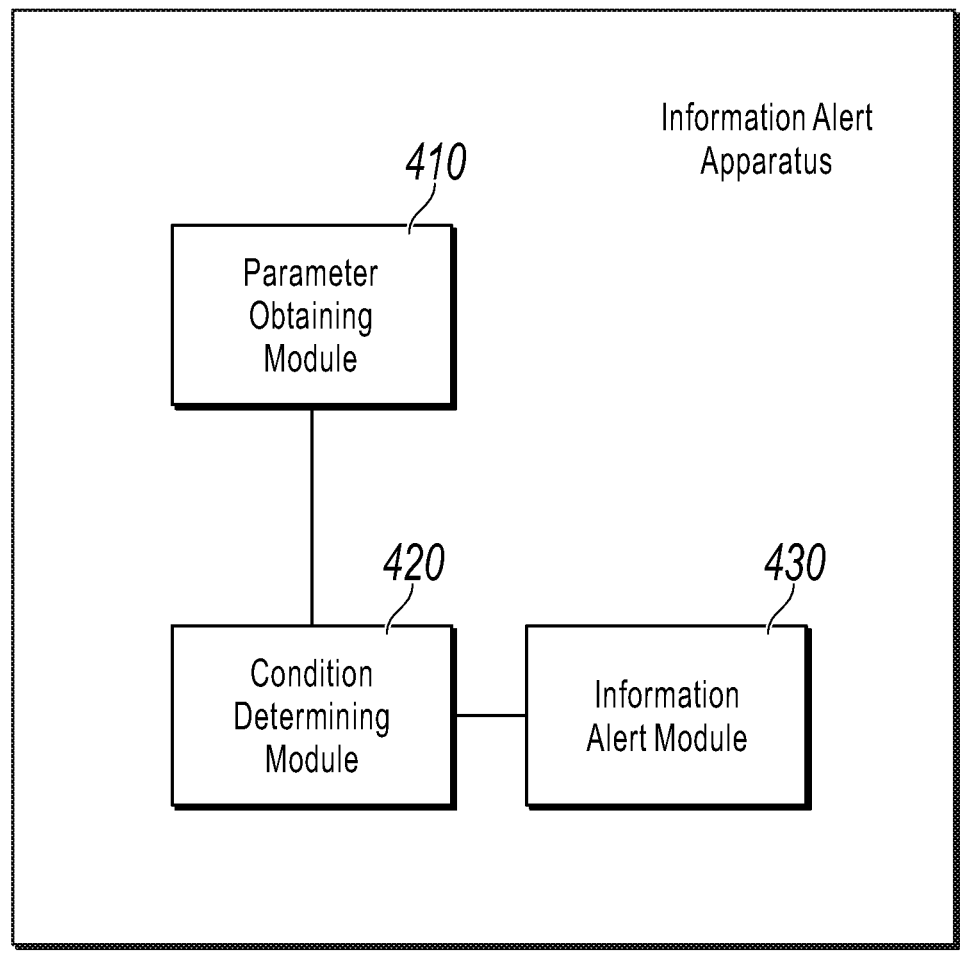
FIG. 4 is a block diagram of an information alert apparatus according to an example embodiment of the present disclosure.

FIG. 4 illustrates a block diagram of an information alert apparatus according to an example embodiment of the present disclosure, the apparatus includes: a parameter obtaining module 410 configured to, when detecting a preset alert trigger event, obtain a physiological characteristic parameter for characterizing an emotion of a target user; a condition determining module 420 configured to determine whether a preset normal emotion fluctuation condition is satisfied according to the physiological characteristic parameter; an information alert module 430 configured to, when it is determined that the normal emotion fluctuation condition is not satisfied, perform a risk alert on the wealth management action of the target user.

In an optional implementation, the preset alert trigger event includes one or more of: receiving an instruction to start a wealth management application; receiving an instruction to display a page of a wealth management product; receiving an instruction to perform a wealth management behavior; a characteristic indicator of the wealth management product on the currently displayed page of the wealth management product is not within a preset indicator range, and the characteristic indicator including rising and falling rates or a rate of return; a risk type of a wealth management product on the currently displayed page of the wealth management product is a preset risk type.

In an optional implementation, the apparatus is provided in a smart terminal, and the parameter obtaining module 410 is configured to: when detecting a preset alert trigger event, obtain a physiological characteristic parameter for characterizing an emotion of a target user from a wearable device bound to the smart terminal.

In an optional implementation, the physiological characteristic parameter includes one or more of: heart rate, body temperature, blood pressure, palm humidity, brain waves, and a facial image.

In an optional implementation, the physiological characteristic parameter includes one or more of heart rate, body temperature, blood pressure, and a palm humidity, and the preset normal emotion fluctuation condition includes: the physiological characteristic parameter is within a normal parameter range; the preset normal parameter range is obtained based on an average value of a physiological characteristic parameter of the user in a specified period; or the preset normal parameter range is obtained based on a physiological characteristic parameter of a user when performing a preset normal type of network behavior; the user includes the target user and/or a user related to the target user, and the relevance includes one or more of the same age group, the same gender, or the same region.

In an optional implementation, the physiological characteristic parameter includes brain waves, and the preset normal emotion fluctuation condition includes: the brain waves having a frequency within a preset normal frequency range, and amplitudes within a preset normal amplitude range.

In an optional implementation, the physiological characteristic parameter includes a facial image, and the condition determination module 420 is configured to: perform expression recognition on the facial image to obtain a facial expression of the target user; determine whether the obtained facial expression is a preset normal type expression.

As for the apparatus embodiment, since it basically corresponds to the method embodiment, the relevant part may refer to the description of the method embodiment. The apparatus embodiments described above are only schematic, and the modules described as separate components may or may not be physically separated, and the components displayed as modules may or may not be physical modules, that is, may be located in one place, or can be distributed to multiple network modules. Some or all of these modules can be selected according to actual needs to achieve the purpose of the solution in the present disclosure. Those of ordinary skill in the art can understand and implement without creative efforts.

Accordingly, an embodiment of the present disclosure further provides a computer device, including: a processor; a memory for storing processor-executable instructions; wherein the processor is configured to: when detecting a preset alert trigger event, obtain a physiological characteristic parameter for characterizing an emotion of a target user; determine whether a preset normal emotion fluctuation condition is satisfied according to the physiological characteristic parameter; when it is determined that the normal emotion fluctuation condition is not satisfied, perform a risk alert on the wealth management action of the target user.

It should be understood that the processor may be further configured to execute the steps of any one of the above information alert method, which will not be elaborated herein.

Each embodiment in the present disclosure is described in a progressive manner, and the same or similar parts between the various embodiments may can refer to each other. Each embodiment focuses on the differences from other embodiments. In particular, as for the device embodiment, since it is basically similar to the method embodiment, the description is relatively simple, and the relevant part may refer to the description of the method embodiment.

A computer storage medium stores g program instructions in the storage medium, the program instructions including: when detecting a preset alert trigger event, obtaining a physiological characteristic parameter for characterizing an emotion of a target user; determining whether a preset normal emotion fluctuation condition is satisfied according to the physiological characteristic parameter; when it is determined that the normal emotion fluctuation condition is not satisfied, performing a risk alert on the wealth management action of the target user.

It can be understood that the program instructions can also perform the steps of any of the above information alert method, which will not be elaborated herein.

The embodiments of the present disclosure may take the form of a computer program product implemented on one or more storage media (including but not limited to a disk storage, a CD-ROM, an optical storage, etc.) containing program codes. Computer-usable storage media includes transitory and non-transitory, removable and non-removable media, and information can be stored by any method or technology. Information can be computer-readable instructions, data structures, modules of a program, or other data. Examples of computer storage media include, but are not limited to: a phase change memory (PRAM), a static random access memory (SRAM), a dynamic random access memory (DRAM), an other types of random access memory (RAM), a read-only memory (ROM), an electrically erasable programmable read-only memory (EEPROM), a flash memory or other memory technologies, a read-only disc, a read-only memory (CD-ROM), a digital versatile disc (DVD) or other optical storage, a magnetic tape cartridge, a magnetic tape storage or other magnetic storage devices or any other non-transmitting medium which can be used to store information that can be accessed by a computing device.

Those skilled in the art can think of other implementations of the present specification after considering the specification and practice of the present disclosure herein. The present disclosure is intended to cover any variations, uses, modification or adaptations of the present disclosure that follow the general principles of the present specification and include common knowledge or conventional technical methods in the related art that are not disclosed in the present disclosure. The specification and implementations are considered as examples only, true scope and spirit of the present disclosure is indicated by the following claims.

It should be understood that the present disclosure is not limited to the precise structure described above and shown in the accompanying drawings, and various modifications and changes can be made without departing from the scope of the present specification. The scope of the present disclosure is limited only by the appended claims.

The above description is merely some but not all implementations of the present disclosure, and is not intended to limit the present disclosure. Any modification, equivalent replacement, or improvement made within the spirit and principles of the present disclosure shall fall within the scope of the present disclosure.

What is claimed is:

1. A computer-implemented information alert method, comprising:
   detecting a preset alert trigger event associated with a wealth management application operated on an electronic device, wherein the preset alert trigger event comprises at least one of:
      receiving an instruction from a target user to perform a wealth management action associated with a wealth management product displayed in the wealth management application, and
      a characteristic indicator of the wealth management product output to a display is not within a preset indicator range, the characteristic indicator of the wealth management product characterizing a performance of one or more assets of the wealth management product;
   in response to detecting the preset alert trigger event, periodically obtaining, by the electronic device, a physiological characteristic parameter from a physiological sensor;
   determining, by the electronic device, that a preset normal emotion fluctuation condition is not satisfied according to the physiological characteristic parameter;
   in response to determining that the preset normal emotion fluctuation condition is not satisfied, determining, by the electronic device, a particular preset risk type from a plurality of preset risk types, each associated with the wealth management action;
   outputting, by the electronic device, a risk alert message associated with the particular preset risk type; after outputting the risk alert message, determining, by the electronic device, that the preset normal emotion fluctuation condition is satisfied according to the physiological characteristic parameter;
   in response to determining that the preset normal emotion fluctuation condition is satisfied, cancelling the outputting of the risk alert message and outputting a normal emotion alert message associated with the preset normal emotion fluctuation condition.

2. The method according to claim 1, wherein the preset alert trigger event comprises at least one of:
   receiving an instruction to start the wealth management application; and
   receiving an instruction to display a page of the wealth management product,
   wherein the characteristic indicator of the wealth management product comprises at least one of a rising rate, a falling rate, and a rate of return.

3. The method according to claim 1, wherein the electronic device is a smart terminal, and
   wherein the physiological sensor is a wearable device bound to the smart terminal.

4. The method according to claim 1, wherein the physiological characteristic parameter comprises at least one of:
   heart rate, body temperature, blood pressure, palm humidity, brain waves, and a facial image.

5. The method according to claim 1, wherein:
   the physiological characteristic parameter comprises at least one of heart rate, body temperature, blood pressure, and palm humidity;
   the preset normal emotion fluctuation condition comprises the physiological characteristic parameter is within a normal parameter range;
   the normal parameter range is obtained based on an average value of either the physiological characteristic parameter of the target user or of a related user physiological characteristic parameter in a specified period, or the normal parameter range is obtained based on either the physiological characteristic parameter of the target user or the related user physiological characteristic parameter when performing a preset normal type of network action; and
   the related user is a user related to the target user who is in a same age group, has a same gender, or is in a same region as the target user.

6. The method according to claim 4, wherein the physiological characteristic parameter comprises brain waves, and wherein the preset normal emotion fluctuation condition comprises:
   frequencies of the brain waves are within a preset normal frequency range and amplitudes of the brain waves are within a preset normal amplitude range.

7. The method according to claim 4, wherein the physiological characteristic parameter comprises a facial image, and wherein determining that the preset normal emotion fluctuation condition is not satisfied comprises:
   obtaining a facial expression of the target user by performing expression recognition on the facial image; and
   determining that the facial expression is not a preset normal type expression.

8. A non-transitory, computer-readable medium storing one or more instructions executable by a computer system to perform operations comprising:
   detecting a preset alert trigger event associated with a wealth management application operated on an electronic device, wherein the preset alert trigger event comprises at least one of
      receiving an instruction from a target user to perform a wealth management action associated with a wealth management product displayed in the wealth management application, and
      a characteristic indicator of the wealth management product output to a display is not within a preset indicator range, the characteristic indicator of the wealth management product characterizing a performance of one or more assets of the wealth management product;
   in response to detecting the preset alert trigger event, periodically obtaining, by the electronic device, a physiological characteristic parameter from a physiological sensor
   determining that a preset normal emotion fluctuation condition is not satisfied according to the physiological characteristic parameter;
   in response to determining that the preset normal emotion fluctuation condition is not satisfied, determining a particular preset risk type from a plurality of preset risk types, each associated with the wealth management action;
   outputting a risk alert message associated with the particular preset risk type;
   after outputting the risk alert message, determining that the preset normal emotion fluctuation condition is satisfied according to the physiological characteristic parameter;
   in response to determining that the preset normal emotion fluctuation condition is satisfied, cancelling the outputting of the risk alert message and outputting a normal emotion alert message associated with the preset normal emotion fluctuation condition.

9. The non-transitory, computer-readable medium according to claim 8, wherein the preset alert trigger event comprises at least one of:

receiving an instruction to start the wealth management application; and receiving an instruction to display a page of the wealth management product, wherein the characteristic indicator of the wealth management product comprises at least one of a rising rate, a falling rate, and a rate of return.

10. The non-transitory, computer-readable medium according to claim 8, wherein the electronic device is a smart terminal, and wherein the physiological sensor is a wearable device bound to the smart terminal.

11. The non-transitory, computer-readable medium according to claim 8, wherein the physiological characteristic parameter comprises at least one of:

heart rate, body temperature, blood pressure, palm humidity, brain waves, and a facial image.

12. The non-transitory, computer-readable medium according to claim 8, wherein:

the physiological characteristic parameter comprises at least one of heart rate, body temperature, blood pressure, and palm humidity;

the preset normal emotion fluctuation condition comprises the physiological characteristic parameter is within a normal parameter range;

the normal parameter range is obtained based on an average value of either the physiological characteristic parameter of the target user or of a related user physiological characteristic parameter in a specified period or the normal parameter range is obtained based on either the physiological characteristic parameter of the target user or the related user physiological characteristic parameter when performing a preset normal type of network action; and the related user is a user related to the target user who is in a same age group, has a same gender, or is in a same region as the target user.

13. The non-transitory, computer-readable medium according to claim 11, wherein the physiological characteristic parameter comprises brain waves, and wherein the preset normal emotion fluctuation condition comprises:

frequencies of the brain waves are within a preset normal frequency range and amplitudes of the brain waves are within a preset normal amplitude range.

14. The non-transitory, computer-readable medium according to claim 11, wherein the physiological characteristic parameter comprises a facial image, and wherein determining that the preset normal emotion fluctuation condition is not satisfied comprises:

obtaining a facial expression of the target user by performing expression recognition on the facial image; and determining that the facial expression is not a preset normal type expression.

15. A computer-implemented system, comprising:

one or more computers; and one or more computer memory devices interoperably coupled with the one or more computers and having tangible, non-transitory, machine-readable media storing one or more instructions that, when executed by the one or more computers, perform one or more operations comprising:

detecting a preset alert trigger event associated with a wealth management application operated on an electronic device, wherein the preset alert trigger event comprises at least one of receiving an instruction from a target user to perform a wealth management action associated with a wealth management product displayed in the wealth management application, and a characteristic indicator of the wealth management product output to a display is not within a preset indicator range, the characteristic indicator of the wealth management product characterizing a performance of one or more assets of the wealth management product;

in response to detecting the preset alert trigger event, periodically obtaining, by the electronic device, a physiological characteristic parameter from a physiological sensor determining that a preset normal emotion fluctuation condition is not satisfied according to the physiological characteristic parameter;

in response to determining that the preset normal emotion fluctuation condition is not satisfied, determining a particular preset risk type from a plurality of preset risk types, each associated with the wealth management action;

outputting a risk alert message associated with the particular preset risk type;

after outputting the risk alert message, determining that the preset normal emotion fluctuation condition is satisfied according to the physiological characteristic parameter;

in response to determining that the preset normal emotion fluctuation condition is satisfied, cancelling the outputting of the risk alert message and outputting a normal emotion alert message associated with the preset normal emotion fluctuation condition.

16. The computer-implemented system according to claim 15, wherein the preset alert trigger event comprises at least one of:

receiving an instruction to start the wealth management application; and receiving an instruction to display a page of the wealth management product, wherein the characteristic indicator of the wealth management product comprises at least one of a rising rate, a falling rate, and a rate of return.

17. The computer-implemented system according to claim 15, wherein the electronic device is a smart terminal, and wherein the physiological sensor is a wearable device bound to the smart terminal.

18. The computer-implemented system according to claim 15, wherein the physiological characteristic parameter comprises at least one of:

heart rate, body temperature, blood pressure, palm humidity, brain waves, and a facial image.

19. The computer-implemented system according to claim 15, wherein:

the physiological characteristic parameter comprises at least one of heart rate, body temperature, blood pressure, and palm humidity;

the preset normal emotion fluctuation condition comprises the physiological characteristic parameter is within a normal parameter range;

the normal parameter range is obtained based on an average value of either the physiological characteristic parameter of the target user or of a related user physiological characteristic parameter in a specified period or the normal parameter range is obtained based on either the physiological characteristic parameter of the target user or the related user physiological characteristic parameter when performing a preset normal type of network action; and the related user is a user related to the target user who is in a same age group, has a same gender, or is in a same region as the target user.

20. The computer-implemented system according to claim 18, wherein the physiological characteristic parameter comprises brain waves, and wherein the preset normal emotion fluctuation condition comprises:

frequencies of the brain waves are within a preset normal frequency range and amplitudes of the brain waves are within a preset normal amplitude range.

* * * * *